(12) United States Patent
Pelati et al.

(10) Patent No.: US 7,919,661 B2
(45) Date of Patent: Apr. 5, 2011

(54) METHOD FOR PRODUCTION OF STYRENE FROM TOLUENE AND SYNGAS

(75) Inventors: Joseph E. Pelati, Houston, TX (US); James R. Butler, League City, TX (US)

(73) Assignee: Fina Technology, Inc., Houston, TX (US)

(*) Notice: Subject to any disclaimer, the term of this patent is extended or adjusted under 35 U.S.C. 154(b) by 421 days.

(21) Appl. No.: 12/193,688

(22) Filed: Aug. 18, 2008

(65) Prior Publication Data
US 2010/0041931 A1    Feb. 18, 2010

(51) Int. Cl.
*C07C 1/32* (2006.01)
*C07C 1/20* (2006.01)

(52) U.S. Cl. .......... 585/469; 585/436; 585/437
(58) Field of Classification Search ............ 585/469, 585/436, 437
See application file for complete search history.

(56) References Cited

U.S. PATENT DOCUMENTS

| | | | |
|---|---|---|---|
| 4,499,318 A | * | 2/1985 | Liu |
| 6,388,159 B1 | | 5/2002 | Jan et al. |
| 6,459,006 B1 | | 10/2002 | Ou et al. |
| 2004/0097769 A1 | * | 5/2004 | Ou et al. ............ 585/454 |
| 2004/0220285 A1 | | 11/2004 | Boerrigter et al. |
| 2008/0184915 A1 | * | 8/2008 | Tonkovich et al. |

* cited by examiner

*Primary Examiner* — Thuan Dinh Dang
(74) *Attorney, Agent, or Firm* — Bradley A. Misley

(57) ABSTRACT

A method for the production of styrene comprising reacting toluene and syngas in one or more reactors is disclosed.

15 Claims, 3 Drawing Sheets

METHOD FOR PRODUCTION OF STYRENE FROM TOLUENE AND SYNGAS

CROSS-REFERENCE TO RELATED APPLICATIONS

Not applicable.

FIELD

The present invention relates generally to the production of styrene.

BACKGROUND

Styrene is an important monomer used in the manufacture of many plastics. Styrene is commonly produced by making ethylbenzene, which is then dehydrogenated to produce styrene. Ethylbenzene is typically formed by one or more aromatic conversion processes involving the alkylation of benzene.

Aromatic conversion processes, which are typically carried out utilizing a molecular sieve type catalyst, are well known in the chemical processing industry. Such aromatic conversion processes include the alkylation of aromatic compounds such as benzene with ethylene to produce alkyl aromatics such as ethylbenzene. Typically an alkylation reactor, which can produce a mixture of monoalkyl and polyalkyl benzenes, will be coupled with a transalkylation reactor for the conversion of polyalkyl benzenes to monoalkyl benzenes. The transalkylation process is operated under conditions to cause disproportionation of the polyalkylated aromatic fraction, which can produce a product having an enhanced ethylbenzene content and reduced polyalkylated content. When both alkylation and transalkylation processes are used, two separate reactors, each with its own catalyst, can be employed for each of the processes.

Ethylene is obtained predominantly from the thermal cracking of hydrocarbons, such as ethane, propane, butane, or naphtha. Ethylene can also be produced and recovered from various refinery processes. Thermal cracking and separation technologies for the production of relatively pure ethylene can account for a significant portion of the total ethylbenzene production costs.

Benzene can be obtained from the hydrodealkylation of toluene that involves heating a mixture of toluene with excess hydrogen to elevated temperatures (for example 500° C. to 600° C.) in the presence of a catalyst. Under these conditions, toluene can undergo dealkylation according to the chemical equation: $C_6H_5CH_3 + H_2 \rightarrow C_6H_6 + CH_4$. This reaction requires energy input and as can be seen from the above equation, produces methane as a byproduct, which is typically separated and may used as heating fuel for the process.

In view of the above, it would be desirable to have a process of producing styrene that does not rely on thermal crackers and expensive separation technologies as a source of ethylene. It would further be desirable to avoid the process of converting toluene to benzene with its inherent expense and loss of a carbon atom to form methane. It would be desirable to produce styrene without the use of benzene and ethylene as feedstreams.

Alternatively, toluene has been used to produce styrene with either methanol or methane/oxygen as the co-feed. Theoretically methanol ($CH_3OH$) and toluene ($C_6H_5CH_3$) can be reacted together to form styrene, water and hydrogen gas, as shown below:

$$CH_3OH + C_6H_5CH_3 \rightarrow C_8H_8 + H_2O + H_2$$

In practice, however, the methanol ($CH_3OH$) often dehydrogenates into formaldehyde ($CH_2O$) and hydrogen gas ($H_2$). Often the toluene conversion is low or the methanol reacts too rapidly and the selectivity on the methanol is too low to make the process economical. In order to avoid this undesirable side reaction, a method of producing styrene without the use of methanol would be desirable.

SUMMARY

Embodiments of the present invention generally include a process for making styrene comprising reacting toluene and synthesis gas, or syngas, comprising a mixture of carbon monoxide (CO) and hydrogen ($H_2$), to form a first product stream comprising styrene. The first product stream can further comprise one or more of benzene, toluene, xylene, water, hydrogen, carbon monoxide, or methane. The process can include at least partially separating the first product stream to form a styrene product stream. Toluene can be separated from the first product stream and recycled to the one or more reactors.

The one or more reactors can have a reaction zone under reaction conditions containing a catalyst for reacting toluene and syngas to form styrene. The reaction zone conditions can be at temperatures ranging from 200° C. to 800° C. and at pressures of from 1 atm to 400 atm or higher. The catalyst can be basic or neutral and can be a basic or neutral zeolite catalyst.

The process can include generating syngas from a carbonaceous material. The syngas can be generated by the partial oxidation of methane, the steam reforming of methane or combinations thereof. Syngas can also be generated by the partial oxidation of coal, the steam reforming of coal or combinations thereof or alternately the partial oxidation of biomass, the steam reforming of biomass or combinations thereof. Syngas can further be generated by the gasification of a carbonaceous material.

DETAILED DESCRIPTION

Figure 1:
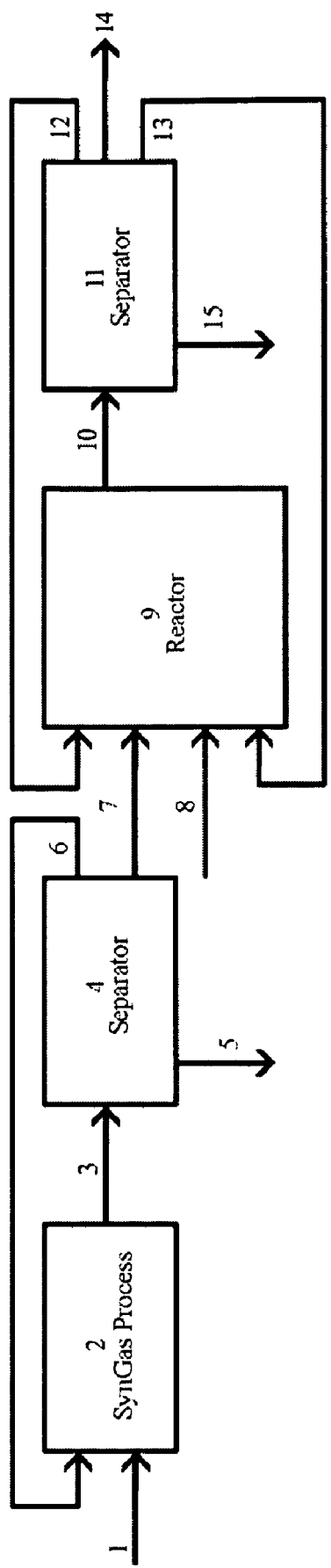
FIG. 1 illustrates a flow chart for the production of styrene by the generation of syngas in a process, the separation of syngas from byproducts (if required), the reaction of syngas and toluene to produce a first product stream comprising styrene, which is sent to a separation unit to purify the styrene stream.

Toluene can be used to produce styrene with the use of syngas as a co-feed wherein the syngas reacts in a side chain alkylation of the toluene resulting in styrene production.

In the present invention styrene can be prepared from the catalytic reaction of syngas (CO/H2) with toluene ($C_6H_5CH_3$) to create styrene ($C_8H_8$) and water as shown:

$$C=O + H_2 + C_6H_5CH_3 \rightarrow C_8H_8 + H_2O$$

Toluene and syngas are known to produce xylene over acidic catalysts, the acid sites known to activate the ring carbons. The present invention involves the use of a basic or neutral catalyst, which can also be in combination with a precious metal or equivalent to activate the syngas. Such a catalyst at elevated temperatures and pressures (200° C. to 800° C. and 1 atm to 400 atm) can produce styrene from toluene and syngas. In alternate embodiments the temperature can range from 300° C. to 500° C. and the pressure from 50 atm to 200 atm. In an alternate embodiment the temperature can range from 300° C. to 500° C. and the pressure from 1 atm to 100 atm.

Syngas is often used in common commercial processes, such as in the production of ammonia or methanol. Below are a number of common ways to generate syngas. Syngas can be produced from natural gas (methane/$CH_4$) by the steam reforming of methane in the presence of a catalyst:

$$CH_4 + H_2O \rightarrow C\!\!=\!\!O + 3H_2$$

A partial oxidation process is also known to produce syngas from methane at high temperature and pressure in an oxygen deficient environment.

$$CH_4 + 1/2 O_2 \rightarrow C\!\!=\!\!O + 2H_2$$

Another alternate way to arrive at syngas from methane is through partial oxidation, along with steam reforming:

$$3CH_4 + H_2O + O_2 \rightarrow 3C\!\!=\!\!O + 7H_2$$

Under the correct conditions a carbon source such as coal or coke, will react with water and/or oxygen, creating syngas, such as for example in a coal gasification facility. Coal gasification technology is commercially available from companies such as Shell, GE Energy, and KBR (Kellogg Brown & Root LLC). The reactions are as shown:

$$C + H_2O \rightarrow C\!\!=\!\!O + H_2$$

$$C + 1/2 O_2 \rightarrow C\!\!=\!\!O$$

Other carbonaceous materials can also be used in the generation of syngas, for example biomass, oil shale, tar, asphalt, hydrocarbon based polymeric materials such as thermoplastics and rubbers, heavy hydrocarbon sludge and bottoms products from petroleum refineries and petrochemical plants, and the like.

In all of these syngas generation processes care must be taken to ensure that carbon does not react with oxygen to create $CO_2$.

After carbon and water have reacted to create syngas, the syngas can then be reacted with toluene ($C_6H_5CH_3$) to create styrene ($C_8H_8$) and water as shown:

$$C\!\!=\!\!O + H_2 + C_6H_5CH_3 \rightarrow C_8H_8 + H_2O$$

This reaction has a 1:1 molar ratio of toluene and syngas and may provide a cleaner reaction with fewer byproducts and undesired side reactions than other methods used to produce styrene. In an embodiment the water produced can be recycled into the reaction cycle for the production of the syngas. Although the reaction has a 1:1 molar ratio of toluene and syngas, the ratio of the feedstreams is not limited within the present invention and can vary depending on operating conditions and the efficiency of the reaction system. If excess toluene or syngas is fed to the reaction zone, the unreacted portion can be subsequently separated and recycled back into the process. In one embodiment the ratio of toluene:syngas can range from between 100:1 to 1:100. In alternate embodiments the ratio of toluene:syngas can range between from 50:1 to 1:50; from 20:1 to 1:20; from 10:1 to 1:10; from 5:1 to 1:5; from 2:1 to 1:2.

The use of a basic or neutral catalyst to activate the side-chain of toluene in combination with a precious metal or equivalent to activate the syngas should produce styrene from toluene and syngas at elevated temperatures and pressures, such as for a non-limiting example from 200° C. to 800° C. and from 1 atm to 200 atm in pressure.

Suitable catalysts for the reaction of toluene and syngas can include as non-limiting examples metal oxides such as: CuO; ZnO—CuO; ZnO—CuO—$Al_2O_3$; $CuCr_2O_4$; $ZnCr_2O_3$; or ZnO—CuO—$Cr_2O_3$. Other catalysts that can be used include metals supported on a substrate such as silica or titania, for example: Ru; Rh; Ni; Co; Pd; or Pt. These can also contain promoters such as Mn, Ti, Zr, V, Nb, K, Cs, or Na. Still another group of catalysts that can be used for the present invention include sulfide based catalysts such as: $MoS_2$; $WS_2$; $Mo_2WS_2$; $CoMoS_2$; or $NoMoS_2$. These sulfide catalysts can include promoters such as K, Rb, Cs, Ca, Sr, Ba, La, or Ce.

The above catalysts can have toluene promoters added such as the alkali, alkaline earth, and/or rare earth elements. Other toluene promoters that can be added include Y, Zr, and/or Nb.

Improvement in side chain alkylation selectivity may be achieved by treating a molecular sieve zeolite material with proper chemical compounds to inhibit the external acidic sites and minimize aromatic alkylation on the ring positions. Another means of improvement of side chain alkylation selectivity can be to impose restrictions on the catalyst structure to facilitate side chain alkylation.

The catalytic reaction systems suitable for this invention can include one or more of the zeolite or amorphous materials modified for side chain alkylation selectivity. A non-limiting example can be a zeolite promoted with one or more of the following: Ru, Rh, Ni, Co, Pd, Pt, Mn, Ti, Zr, V, Nb, K, Cs, or Na which may promote the syngas reactivity with toluene.

Zeolite materials suitable as base materials of catalysts for this invention may include silicate-based zeolites and amorphous compounds such as faujasites, mordenites, pentasils, etc. Silicate-based zeolites are made of alternating $SiO_2$ and $MO_x$ tetrahedra, where M is an element selected from the Groups 1 through 16 of the Periodic Table (new IUPAC). These types of zeolites have 8-, 10-, or 12-membered oxygen ring channels. An example of zeolites suitable for this invention may include 10- and 12-membered ring zeolites, such as ZSM-5, ZSM-11, ZSM-22, ZSM-48, ZSM-57, etc.

FIG. 1 is a simplified block-flow diagram for one embodiment of the styrene production process described above. A carbonaceous material (1) is fed to a process (2), such as a first reactor, that generates syngas. The process (2) provides the partial oxidation, steam reforming, gasification or other process of converting a carbonaceous material to syngas. The process (2) can comprise one or more reactors that can include one or more of the methods for generating syngas mentioned above, or combinations thereof. The gas product (3) of the process (2) may be sent to a separation unit (4) where the syngas (7) is separated from undesirable byproducts (6) that can be recycled to the process (2) and unwanted byproducts (5) that can be removed from the styrene production process. The separation unit (4) can comprise one or more separation stages, such as one or more distillation columns that can be operated at differing conditions for the separation of the components of stream (3). The syngas feed stream (7) is then added along with a feed stream comprising toluene (8) into reactor (9) to produce a product stream (10) comprising styrene. Reactor (9) can comprise one or more reactors and/or reaction zones. The product stream (10) comprising styrene from reactor (9) may then be sent to a separation unit (11) where unwanted byproducts (15) like water can be separated from the styrene and removed from the process or can be recycled back to process (2) if water is used in the production of the syngas, such as in steam reforming processes. The separation unit (11) can comprise one or more separation stages, such as one or more distillation columns that can be operated at differing conditions for the separation of the components of stream (10). The unreacted syngas (12) and the unreacted toluene (13) can be separated and recycled back into the reactor (9). A styrene product stream (14) can be removed from the separation unit (11) and subjected to further treatment or processing if required.

The operating conditions of the reactors and separators will be system specific and can vary depending on the feedstream composition and the composition of the product streams. The reactor (9) for the reaction of toluene and syngas will operate at elevated temperatures and pressures, such as for a non-limiting example from 200° C. to 800° C. and from 1 atm to 200 atm in pressure and will contain a basic or neutral catalyst system. The catalyst system may also a precious metal or equivalent to activate the syngas.

Figure 2:
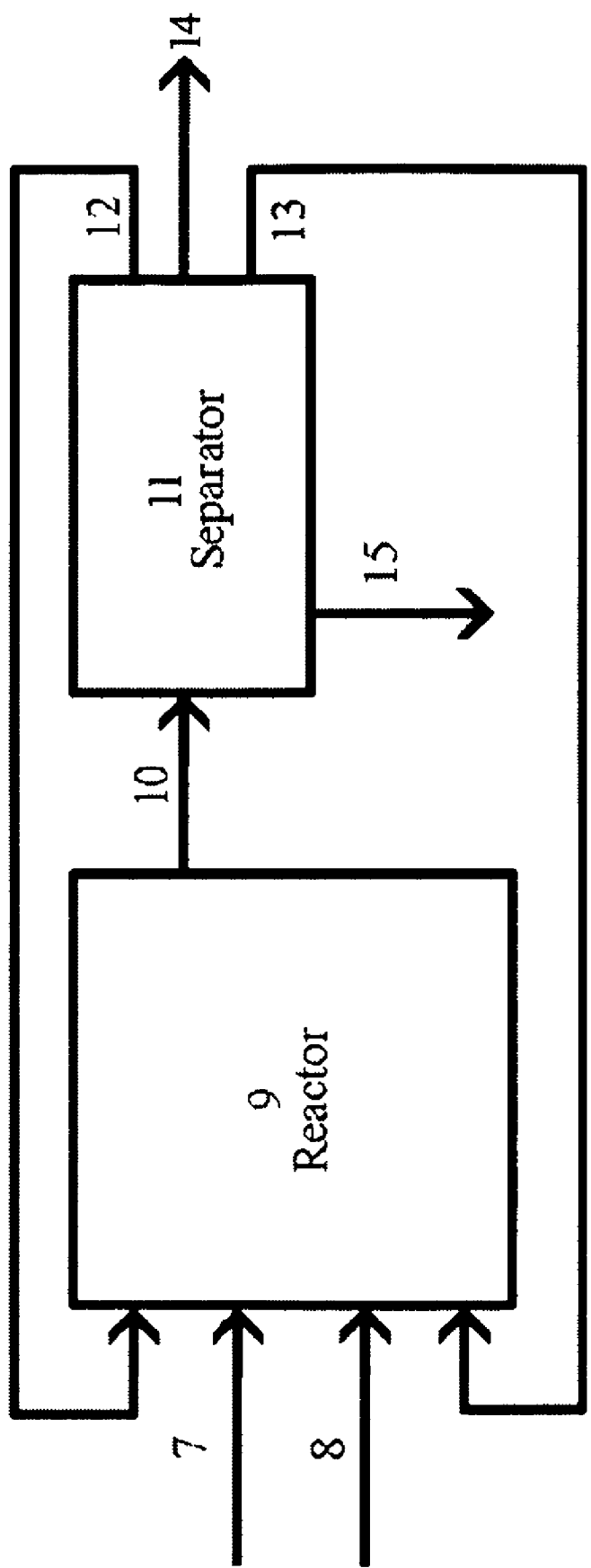
FIG. 2 illustrates a flow chart for the production of styrene by the reaction of syngas and toluene, wherein the syngas and toluene are reacted to produce a product stream comprising styrene, which is sent to a separation unit to purify the styrene stream.

FIG. 2 is a simplified block-flow diagram for an alternate embodiment of the styrene production process. A syngas feed stream (7) is added along with a feed stream comprising toluene (8) into reactor (9) to produce a product stream (10) comprising styrene. Reactor (9) can comprise one or more reactors and/or reaction zones. The product stream (10) comprising styrene from reactor (9) may then be sent to a separation unit (11) where unwanted byproducts (15) like water can be separated from the styrene and removed from the process or can be recycled back to process (2) if water is used in the production of the syngas, such as in steam reforming processes. The separation unit (11) can comprise one or more separation stages, such as one or more distillation columns that can be operated at differing conditions for the separation of the components of stream (10). The unreacted syngas (12) and the unreacted toluene (13) can be separated and recycled back into the reactor (9). A styrene product stream (14) can be removed from the separation unit (11) and subjected to further treatment or processing if required.

Figure 3:
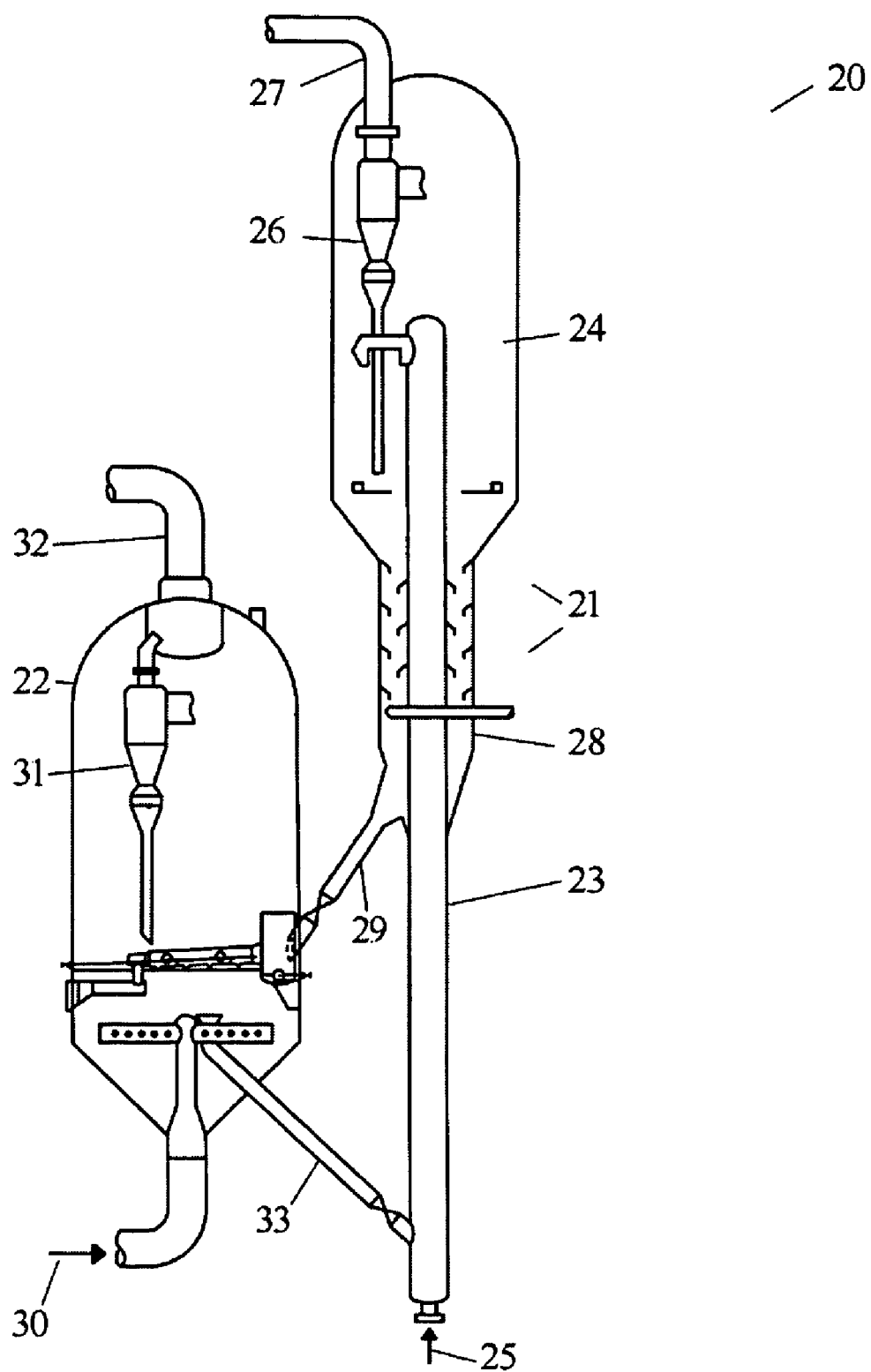
FIG. 3 is a schematic illustration of an aspect of an embodiment of the present invention having the capability for continuous reaction with catalyst regeneration.

Embodiments of reactors that can be used with the present invention can include, by non-limiting examples: fixed bed reactors; fluid bed reactors; and entrained bed reactors. Reactors capable of the elevated temperature and pressure as described herein, and capable of enabling contact of the reactants with the catalyst, can be considered within the scope of the present invention. Embodiments of the particular reactor system may be determined based on the particular design conditions and throughput, as by one of ordinary skill in the art, and are not meant to be limiting on the scope of the present invention. An example of a fluid bed reactor having catalyst regeneration capabilities that may be employed with the present invention is illustrated in FIG. 3. This type of reactor system employing a riser can be modified as needed, for example by insulating or heating the riser if thermal input is needed, or by jacketing the riser with cooling water if thermal dissipation is required. These designs can also be used to replace catalyst while the process is in operation, by withdrawing catalyst from the regeneration vessel from an exit line (not shown) or adding new catalyst into the system while in operation.

FIG. 3 is a schematic illustration of an embodiment of the present invention having the capability for continuous reaction with catalyst regeneration. The reaction process (20) generally comprises two main zones for reaction (21) and regeneration (22). A reaction zone is usually comprised of a vertical conduit, or riser (23), as the main reaction site, with the effluent of the conduit emptying into a large volume process vessel, which may be referred to as a separation vessel (24). In the reaction riser (23), a feed stream (25), such as toluene and syngas, is contacted with a fluidized catalyst, which can be a relatively large fluidized bed of catalyst, at reactor conditions. The residence time of catalyst and hydrocarbons in the riser (23) needed for substantial completion of the reaction may vary as needed for the specific reactor design and throughput design. The flowing vapor/catalyst stream leaving the riser (23) may pass from the riser to a solids-vapor separation device, such as a cyclone (26), normally located within and at the top of the separation vessel (24). The products of the reaction can be separated from the portion of catalyst that is carried by the vapor stream by means of one or more cyclone (26) and the products can exit the cyclone (26) and separation vessel (24) via line (27). The spent catalyst falls downward to a stripper (28) located in a lower part of the separation vessel (24). Catalyst can be transferred to a regeneration vessel (22) by way of a conduit (29) connected to the stripper (28).

The catalyst can be continuously circulated from the reaction zone (21) to the regeneration vessel (22) and then again to the reaction zone (21). The catalyst can therefore act as a vehicle for the transfer of heat from zone to zone as well as providing the necessary catalytic activity. Catalyst from the reaction zone (21) that is being transferred to the regeneration zone (22) can be referred to as "spent catalyst". The term "spent catalyst" is not intended to be indicative of a total lack of catalytic activity by the catalyst particles. Catalyst, which is being withdrawn from the regeneration vessel (22), is referred to as "regenerated" catalyst. The catalyst can be regenerated in the regeneration vessel (22) by heat and contact with a regeneration stream (30). The regeneration stream (30) can comprise oxygen and can comprise steam. The regenerated catalyst can be separated from the regeneration stream by the use of one or more cyclones (31) that can enable the removal of the regeneration vessel (22) via line (32). The regenerated catalyst can be transferred via line (33) to the lower section of the riser (23) where it is again in contact with the feed stream (25) and can flow up the riser (23).

Use of broader terms such as comprises, includes, having, etc. should be understood to provide support for narrower terms such as consisting of, consisting essentially of, comprised substantially of, etc.

The term "alkyl" refers to a functional group or side-chain that consists solely of single-bonded carbon and hydrogen atoms, for example a methyl or ethyl group.

The term "alkylation" refers to the addition of an alkyl group to another molecule.

Use of the term "optionally" with respect to any element of a claim is intended to mean that the subject element is required, or alternatively, is not required. Both alternatives are intended to be within the scope of the claim.

The term "syngas" refers to synthesis gas comprising a mixture of carbon monoxide (CO) and hydrogen ($H_2$).

The term "transalkylation" refers to the transfer of an alkyl group from one aromatic molecule to another.

The term "zeolite" refers to a molecular sieve containing a silicate lattice, usually in association with some aluminum, boron, gallium, iron, and/or titanium, for example. In the following discussion and throughout this disclosure, the terms molecular sieve and zeolite will be used more or less interchangeably. One skilled in the art will recognize that the teachings relating to zeolites are also applicable to the more general class of materials called molecular sieves.

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof and the scope thereof is determined by the claims that follow.

What is claimed is:

1. A process of making styrene comprising:
   Reacting toluene with syngas under reaction conditions in the presence of a catalyst comprising a basic or neutral zeolite and one or more promoters selected from the group consisting of alkali elements, alkaline earth elements, rare earth elements, Y, Zr, and Nb to produce a first product comprising styrene and water.

2. The process of claim 1, wherein the reaction conditions occur at temperatures of 200° C. to 800° C. at pressures of 1 atm to 400 atm.

3. The process of claim 1, further comprising:
   one or more reactors at said reaction conditions containing said catalyst for reacting toluene with syngas to produce styrene and water.

4. The process of claim 1, wherein the first product stream further comprises one or more of benzene, toluene, xylene, water, hydrogen, carbon monoxide, or methane.

5. The process of claim 1, further comprising:
   at least partially separating the first product stream to form a styrene product stream.

6. The process of claim 1, further comprising:
   separated toluene from the first product stream and recycled said toluene to the one or more reactors.

7. The process of claim 1, further comprising:
   generating syngas by the conversion of a carbonaceous material.

8. The process of claim 7, wherein the conversion of a carbonaceous material includes the partial oxidation of methane, the steam reforming of methane, or combinations thereof.

9. The process of claim 7, wherein the conversion of a carbonaceous material includes the partial oxidation of coal or coke, the steam reforming of coal or coke, or combinations thereof.

10. The process of claim 7, wherein the conversion of a carbonaceous material includes the partial oxidation of biomass, the steam reforming of biomass, or combinations thereof.

11. A method for making styrene comprising:
    providing a reaction zone containing a catalyst comprising a basic or neutral zeolite and one or more promoters selected from the group consisting of alkali elements, alkaline earth elements, rare earth elements, Y, Zr, and Nb for reacting toluene and syngas to form styrene;
    reacting toluene and syngas in said reaction zone under reaction conditions to form a first product stream comprising styrene and water;
    at least partially separating the first product stream to form a styrene product stream;
    removing unreacted toluene from the first product stream and recycling the unreacted toluene to the reaction zone.

12. The method of claim 11, wherein the reaction zone conditions are at a temperature between 200° C. to 800° C. and a pressure between 1 atm to 400 atm.

13. The method of claim 11, further comprising:
    generating syngas by the partial oxidation or steam reforming combination thereof of a carbonaceous material.

14. The process of claim 13, wherein the carbonaceous material comprises one or more of methane, coal, coke, biomass or combinations thereof.

15. A method for making styrene comprising:
    generating syngas by the gasification of a carbonaceous material;
    providing a reaction zone containing a catalyst comprising a basic or neutral zeolite and one or more promoters selected from the group consisting of alkali elements, alkaline earth elements, rare earth elements, Y, Zr, and Nb for reacting toluene and syngas to form styrene;
    providing feedstreams of toluene and syngas to the reaction zone;
    reacting toluene and syngas in the reaction zone containing said catalyst at a temperature between 200° C. to 800° C. and a pressure between 1 atm to 400 atm to form a first product stream comprising styrene and water;
    at least partially separating the first product stream to form a styrene product stream;
    removing unreacted toluene from the first product stream and recycling said unreacted toluene to the reaction zone.

* * * * *